(12) United States Patent  
Vad et al.

(10) Patent No.: US 9,351,860 B2  
(45) Date of Patent: May 31, 2016

(54) LOADING TOOL FOR CAPTURING STENT POINTS

(71) Applicant: Cook Medical Technologies LLC, Bloomington, IN (US)

(72) Inventors: Siddharth Vad, Bloomington, IN (US); Rick Hadley, Otterbein, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 532 days.

(21) Appl. No.: 13/827,789

(22) Filed: Mar. 14, 2013

(65) Prior Publication Data

US 2014/0277336 A1  Sep. 18, 2014

(51) Int. Cl.
*A61F 2/966* (2013.01)
*A61F 2/95* (2013.01)

(52) U.S. Cl.
CPC . *A61F 2/95* (2013.01); *A61F 2/966* (2013.01); *A61F 2002/9522* (2013.01); *A61F 2002/9665* (2013.01)

(58) Field of Classification Search
CPC .. A61F 2/88–2/90; A61F 2/95; A61F 2/2436; A61F 2002/9517; A61F 2002/9505; A61F 2002/9665; A61F 2002/9522
See application file for complete search history.

(56) References Cited

U.S. PATENT DOCUMENTS

| | | | |
|---|---|---|---|
| 5,562,726 A * | 10/1996 | Chuter | 623/1.35 |
| 5,749,921 A | 5/1998 | Lenker et al. | |
| 5,868,779 A * | 2/1999 | Ruiz | 606/194 |
| 5,911,752 A | 6/1999 | Dustrude et al. | |
| 6,096,027 A | 8/2000 | Layne | |
| 6,132,458 A | 10/2000 | Staehle et al. | |
| 6,149,680 A | 11/2000 | Shelso et al. | |
| 6,391,050 B1 | 5/2002 | Broome | |
| 6,471,718 B1 | 10/2002 | Staehle et al. | |
| 6,506,178 B1 * | 1/2003 | Schubart et al. | 604/93.01 |
| 6,572,643 B1 * | 6/2003 | Gharibadeh | 623/1.11 |
| 6,776,791 B1 * | 8/2004 | Stallings et al. | 623/1.11 |
| 6,858,034 B1 | 2/2005 | Hijlkema et al. | |
| 6,926,732 B2 | 8/2005 | Derus et al. | |
| 6,939,370 B2 | 9/2005 | Hartley et al. | |
| 7,264,632 B2 | 9/2007 | Wright et al. | |
| 7,435,253 B1 | 10/2008 | Hartley et al. | |

(Continued)

FOREIGN PATENT DOCUMENTS

| | | |
|---|---|---|
| EP | 1 369 098 A1 | 12/2003 |
| EP | 1 400 219 A1 | 3/2004 |

(Continued)

*Primary Examiner* — Lee D Wilson
*Assistant Examiner* — Tyrone V Hall, Jr.
(74) *Attorney, Agent, or Firm* — Brinks Gilson & Lione (57) ABSTRACT

The present embodiments provide systems and methods for loading a stent or stent graft onto an introducer for intraluminal deployment. In one example, a system includes an endoluminal prosthesis introducer comprising a stent retaining member engageable with a stent end. The system may also include a loading tool for engaging the stent end on the stent retaining member. The loading tool may include a loading body having a passage extending from a first end to a second end and a slot that extends through the tubular loading body from the passage to an outer surface of the tubular loading body, and the slot may further extend from the second end toward the first end. The stent retaining member may be disposed at least partially within the passage of the loading body, and the slot of the loading body may be rotatable around the stent retaining member.

20 Claims, 9 Drawing Sheets

(56) References Cited

U.S. PATENT DOCUMENTS

| | | |
|---|---|---|
| 7,763,063 B2 | 7/2010 | Arbefeuille et al. |
| 7,763,066 B2 | 7/2010 | Parker |
| 7,771,463 B2 | 8/2010 | Ton et al. |
| 7,815,670 B2 | 10/2010 | Austin et al. |
| 7,918,880 B2 | 4/2011 | Austin |
| 8,070,790 B2 | 12/2011 | Berra et al. |
| 8,157,853 B2 | 4/2012 | Laske et al. |
| 2003/0074057 A1 | 4/2003 | Rosengart |
| 2003/0083730 A1 | 5/2003 | Stinson |
| 2004/0260377 A1 | 12/2004 | Flomenblit et al. |
| 2005/0049667 A1 | 3/2005 | Arbefeuille et al. |
| 2005/0166389 A1 | 8/2005 | Perreault et al. |
| 2005/0288766 A1 | 12/2005 | Plain et al. |
| 2006/0004433 A1 | 1/2006 | Greenberg et al. |
| 2006/0058864 A1 | 3/2006 | Schaeffer et al. |
| 2006/0064152 A1 | 3/2006 | Olson |
| 2006/0136034 A1* | 6/2006 | Modesitt et al. ............. 623/1.11 |
| 2006/0136035 A1 | 6/2006 | Hermann et al. |
| 2007/0043419 A1 | 2/2007 | Nikolchev et al. |
| 2007/0203561 A1* | 8/2007 | Forster et al. ................ 623/1.11 |
| 2007/0239271 A1* | 10/2007 | Nguyen ....................... 623/2.11 |
| 2008/0027529 A1 | 1/2008 | Hartley et al. |
| 2008/0082158 A1* | 4/2008 | Tseng et al. ................. 623/1.13 |
| 2009/0054976 A1 | 2/2009 | Tuval et al. |
| 2010/0274187 A1* | 10/2010 | Argentine .................. 604/96.01 |
| 2010/0298931 A1 | 11/2010 | Quadri et al. |
| 2011/0137401 A1 | 6/2011 | Dorn et al. |
| 2011/0144735 A1 | 6/2011 | Hartley et al. |
| 2011/0178588 A1 | 7/2011 | Haselby |
| 2011/0251667 A1 | 10/2011 | Argentine |
| 2011/0257720 A1 | 10/2011 | Peterson et al. |
| 2012/0239142 A1* | 9/2012 | Liu et al. ..................... 623/2.11 |

FOREIGN PATENT DOCUMENTS

| | | |
|---|---|---|
| EP | 1 982 677 A2 | 10/2008 |
| WO | WO 2009/121006 A1 | 10/2009 |

* cited by examiner

FIG. 10

LOADING TOOL FOR CAPTURING STENT POINTS

TECHNICAL FIELD

This disclosure relates to medical devices and more particularly to a loading tool to load a prosthesis onto an introducer for introducing the prosthesis into a human or animal body.

BACKGROUND

In the deployment of a prosthesis such as a stent or stent graft into the human or animal body via intraluminal techniques, an introducer or delivery device is used to introduce the prosthesis into a vessel or a lumen of the body. After the prosthesis has been deployed and expanded within the lumen, the introducer is withdrawn from the body.

Stents may be inserted into an anatomical vessel or duct for various purposes. Stents may maintain or restore patency in a formerly blocked or constricted passageway, for example, following a balloon angioplasty procedure. Other stents may be used for different procedures. For example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they may have characteristics of both types of stents. Self-expanding stents may be delivered to a target site in a compressed configuration and subsequently expanded by removing a delivery sheath, removing trigger wires, and/or releasing diameter reducing ties. With self-expanding stents, the stents expand primarily based on their own expansive force without the need for further mechanical expansion. In a stent made of a shape memory alloy such as nitinol, the shape memory alloy may be employed to cause the stent to return to a predetermined configuration upon removal of the sheath or other device maintaining the stent in its pre-deployment configuration.

Depending on the configuration of the stent and the introducer, the process to load the stent onto the introducer may be difficult and/or complex. For example, the stent may include a plurality of apices at a stent end that the introducer is configured to capture. However, manipulating the apices by hand in order to have the apices captured by the introducer may be difficult. Therefore, it is desirable to provide an improved method of loading stents onto introducers.

SUMMARY

The present embodiments provide systems and methods for loading a stent or stent graft onto an introducer for intraluminal deployment. In one example, a system includes an endoluminal prosthesis introducer comprising a stent retaining member engageable with a stent end in a compressed configuration. The system may also include a loading tool for engaging the stent end with the stent retaining member. The loading tool may include a loading body having a passage extending from a first end to a second end and a slot that extends through the tubular loading body from the passage to an outer surface of the tubular loading body, and the slot may further extend from the second end toward the first end. The stent retaining member may be disposed at least partially within the passage of the loading body, and the slot of the loading body may be rotatable around the stent retaining member.

In another example, a method of loading a stent end onto an endoluminal prosthesis introducer is provided. The method may include providing an endoluminal prosthesis introducer comprising a stent retaining member engageable with a stent end in a compressed configuration. The method may also include positioning a loading tool comprising a loading body having a passage extending from a first end to a second end such that the engaging member is disposed at least partially within the passage of the loading body. The loading body may also include a slot that extends through the loading body from the passage to an outer surface of the tubular loading body, and the slot may extend from the second end toward the first end. The method may further include rotating the slot of the loading body around the stent retaining member.

In a further example, a loading tool to facilitate engaging a stent end on a stent retaining member is provided. The loading tool can include a loading body having a passage extending from a first end to a second end and a slot that extends through the loading body from the passage to an outer surface of the tubular loading body. The slot can extend from the second end toward the first end. A stent retaining member can be positionable at least partially within the passage of the loading body, and the slot of the loading body can be rotatable around the stent retaining member.

DETAILED DESCRIPTION OF THE DRAWINGS AND THE PRESENTLY PREFERRED EMBODIMENTS

The present disclosure relates to a loading tool to load a prosthesis such as a stent or stent graft onto an introducer for intraluminal deployment of the prosthesis. The embodiments described in this disclosure will be discussed generally in relation to deployment of stent grafts into the aorta, but the disclosure is not so limited and may be applied to other vasculature or other body vessels or lumens.

Loading tools described herein may be configured to load or engage a prosthesis onto an introducer. However, in order to better understand the loading tools, example prostheses and introducers that may be used with the loading tool are described first in Section I below. In Section II below, loading tools and methods of loading prostheses and introducers with a loading tool are described. While specific examples of prostheses and introducers may be described below, it should be understood that the loading tools may be used with other prostheses and introducers. For instance, the loading tools described herein may be used with any of the prostheses and introducers described in U.S. patent application Ser. No. 13/669,145, entitled "Endoluminal Prosthesis Introducer," filed Nov. 5, 2012, which is incorporated by reference herein in its entirety.

In the present disclosure, the term "proximal" refers to a direction that is generally closest to the heart during a medical procedure, while the term "distal" refers to a direction that is farthest from the heart during a medical procedure.

The term "stent graft" refers to a device that has a tubular body of biocompatible graft material and at least one stent fastened to the tubular body to define a lumen through the stent graft. The stent graft may be bifurcated and/or may include fenestrations, side arms, or the like. Other arrangements of stent grafts also are within the scope of this disclosure.

I. Prostheses and Introducers

Figure 1:
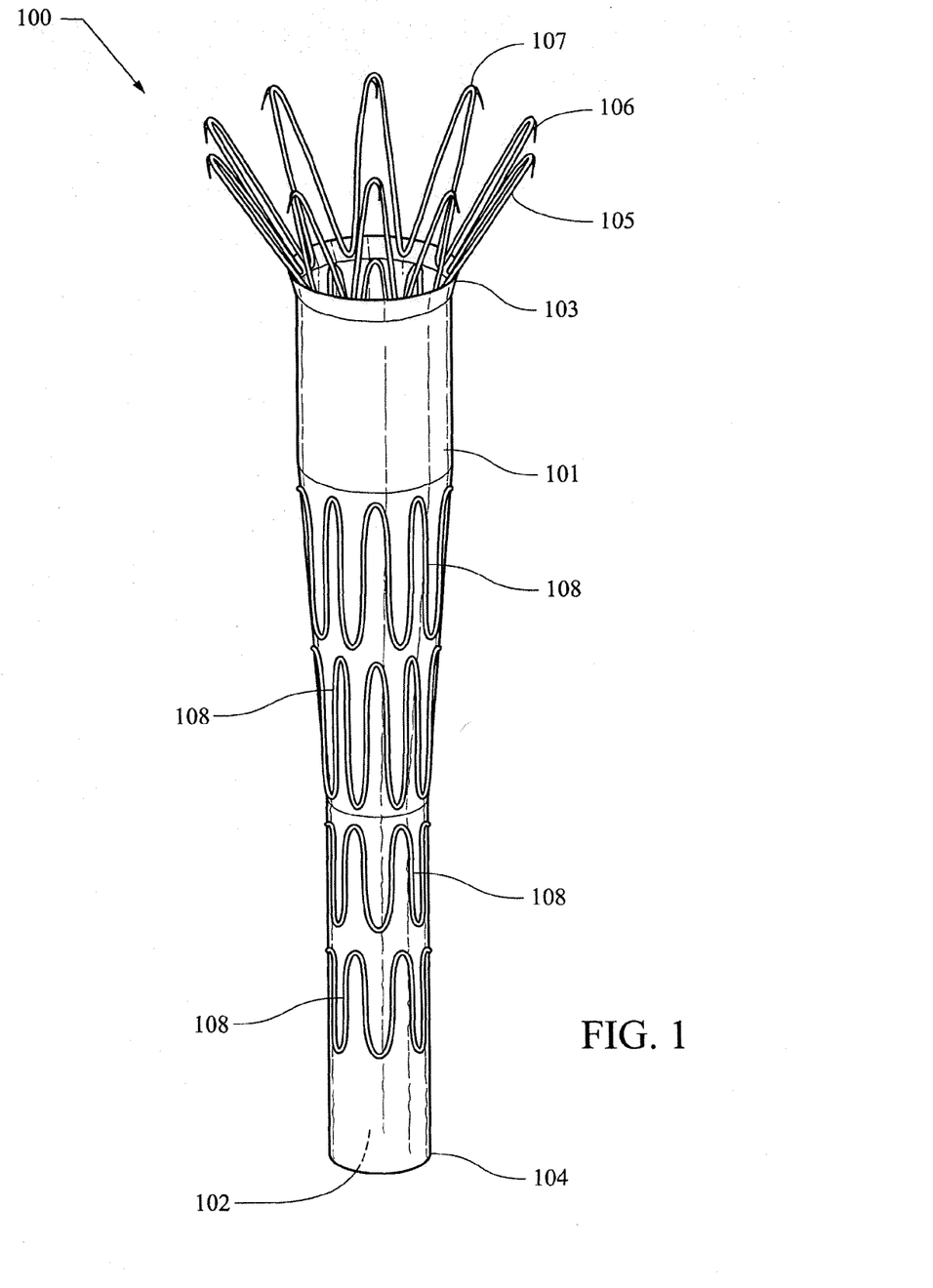
FIG. 1 illustrates one example of a stent graft.

FIG. 1 depicts one embodiment of a stent graft 100 that may be deployed using an introducer or delivery device as further described below. The stent graft 100 may be of a self expanding type having resilient stents to enable the stent graft to expand upon release from the introducer. The stent graft 100 may include a graft body 101 having a generally tapering tubular configuration. In other examples, the graft body 101 may have a generally cylindrical tubular configuration with a substantially constant diameter. The graft body 101 may have a lumen 102 extending longitudinally between a proximal end 103 and a distal end 104 thereof. An attachment stent 105 may extend proximally beyond the proximal end 103 of the graft body 101. Additional stents 108 may be positioned along the length of the graft body 101.

The stent 105 may include distally extending projections 106. The projections 106 may be disposed generally internal or external to the lumen 102 of the stent graft 100. In one example, the projections 106 may be disposed substantially external to the lumen 102 of the stent graft 100 when the stent graft is deployed. The projections 106 may be configured as barbs as shown in FIG. 1. Such barbs may be configured to engage a wall of a body vessel upon deployment of the stent graft from the introducer to fix the stent graft in place relative to the body vessel. Alternatively, the projections 106 may be configured as tabs or any other form of projecting member. Such tabs may be disposed generally internal to the lumen 102 of the stent graft 100 or external to the lumen of the stent graft. In one example, the tabs may be disposed generally along a surface plane of the stent graft 100 upon deployment of the stent graft from the introducer. Such tabs may lie substantially flat against the attachment stent and/or the graft body when the stent graft is deployed. In other words, such tabs may not extend outward from the stent graft to engage the wall of the body vessel upon deployment of the stent graft. The projections 106 may extend from a proximal end 107 of the stent graft 100. The proximal end 107 may be defined by a plurality of bends of the stent 105. If the projections 106 are disposed external to the lumen 102 of the stent graft 100, the projections may be everted to a position generally within the lumen 102 for engagement with a deployment member of the introducer as further described below.

Figure 2:
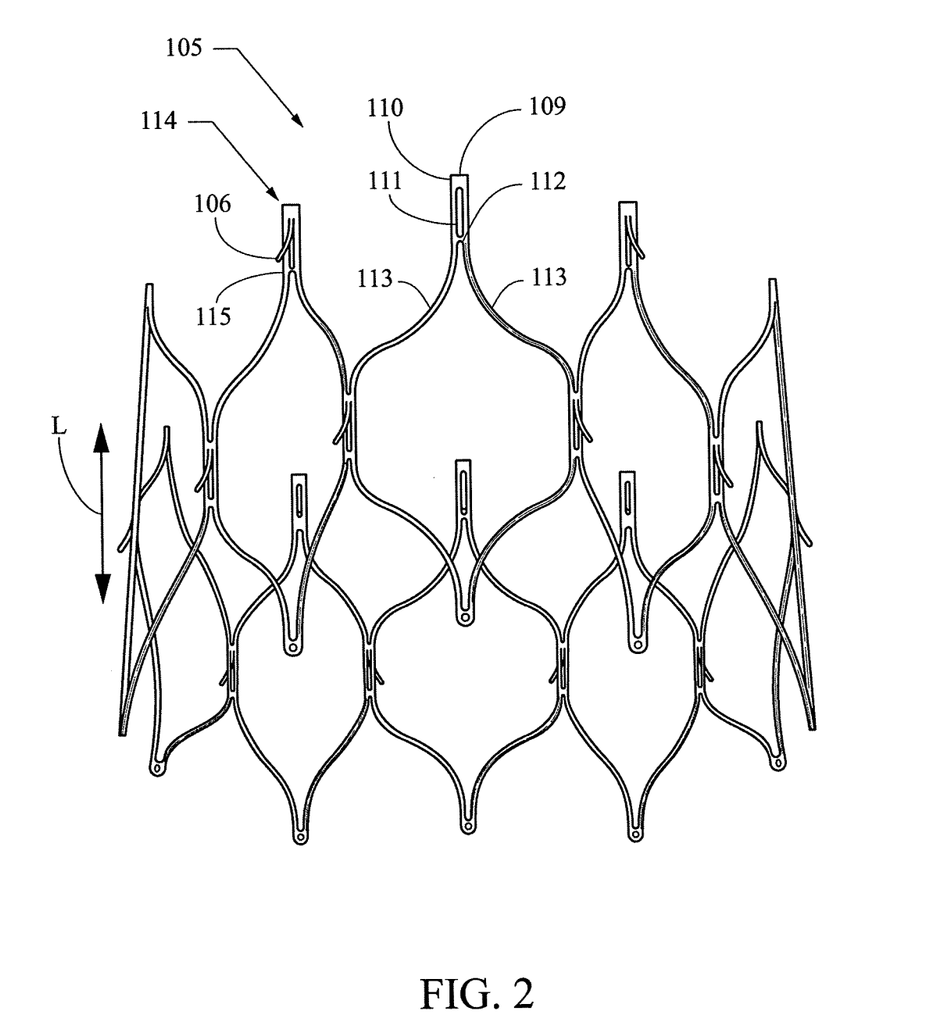
FIG. 2 illustrates one example of an attachment stent.

In one example, the attachment stent 105 may be configured as shown in FIG. 2 and described in U.S. Patent Application Pub. No. 2009/0204202 by Dierking et al., which is incorporated by reference herein in its entirety. For example, the attachment stent 105 may include one or more first proximal apices 109. Each first proximal apex 109 may include an end region 110 having an aperture 111 formed therein. The aperture 111 may be configured to receive a stent engaging member of an introducer as further described below. The end region 110 may be positioned proximal of the bend 112 between two adjacent struts 113 of the stent 105. In other words, the end region 110 may be configured as an eyelet extending proximally from the bend 112 between two adjacent struts 113 to receive the stent engaging member of the introducer. Upon compression of the stent 105, the stent engaging member may not be pinched between the adjacent struts of the stent. In other words, the eyelet may remain open even after compression of the stent 105. This may avoid damage to the struts 113 which may be caused by pinching the stent engaging member between the struts.

Additionally, or alternatively, the attachment stent 105 may include one or more second proximal apices 114. Each second proximal apex 114 may include an end region 115 having an integral barb 106 formed therein. The barb 106 may be configured to engage a wall of a body vessel to prevent migration of the stent graft 100 within the body vessel. The stent 105 may include alternating first proximal apices and second proximal apices, as shown in FIG. 2, so that every other apex may be engaged by a stent engaging member. In other examples, the stent 105 may have any number of first proximal apices and second proximal apices. In one example, each apex of the attachment stent 105 may be configured as a first proximal apex (i.e., each apex may include an end region 110 with an aperture 111). In this manner, each apex of the stent 105 may be engaged by a stent engaging member of the introducer.

Although the operation of the introducer will be described with reference to the stent graft 100, the introducer may be used with a stent or stent graft having any other configuration. For example, the introducer described below may be used for intraluminal deployment of a bifurcated stent graft, a stent graft having one or more branches, scallops, and/or fenestrations, or any other type of stent graft. Additionally, or alternatively, the introducer may be used for intraluminal deployment of a bare stent or any other type of prosthesis including, for example, a self-expanding stent. Such embodiments are contemplated by and within the scope of this disclosure.

Figure 3:
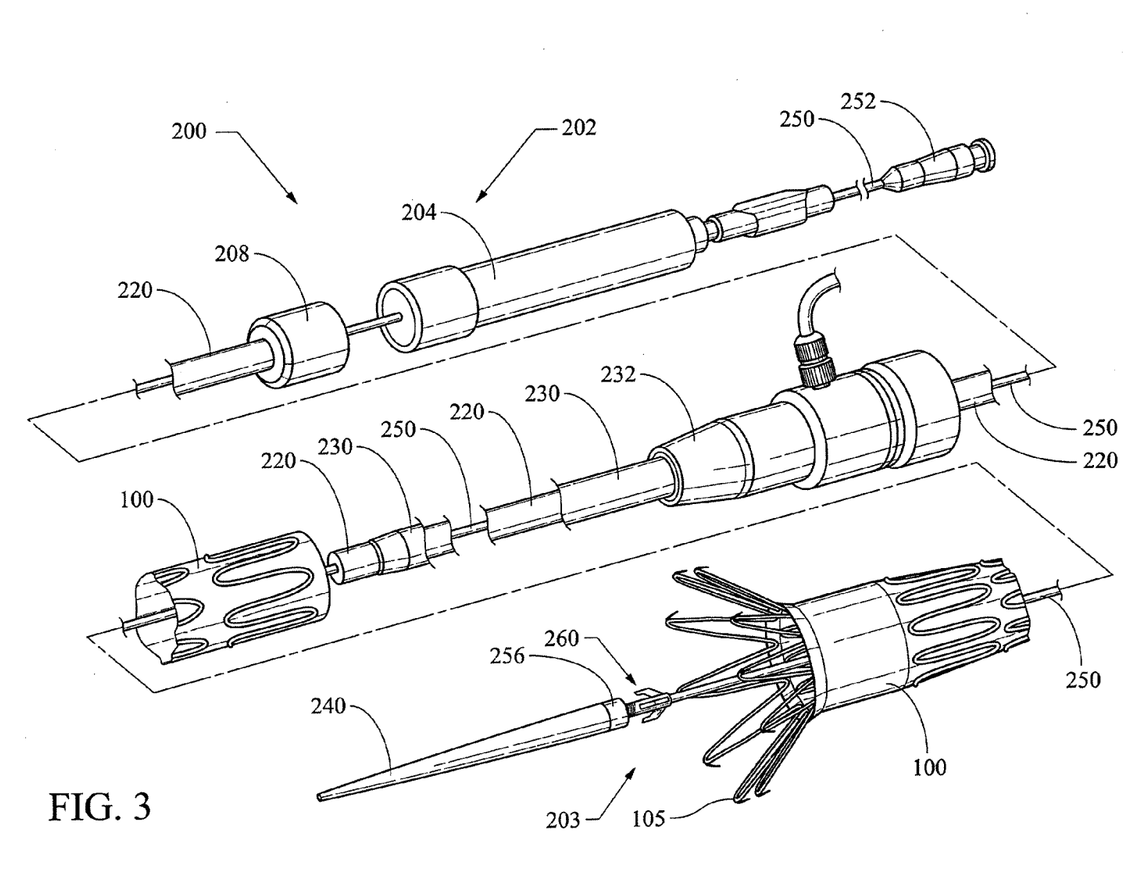
FIG. 3 illustrates one example of an introducer.

FIG. 3 illustrates one example of an introducer 200, which may be used to deliver and deploy a prosthesis (e.g., the stent graft 100) as further described below. The introducer 200 may include a handle portion 202 and an introduction portion 203. The handle portion 202 may remain outside of the patient in use, and the introduction portion 203 may be introduced into the patient via a puncture in an artery such as a femoral artery. The introducer 200 may include a catheter, such as the pusher catheter 220. The pusher catheter 220 may extend proximally from the handle 202. The pusher catheter 220 may be configured as an elongate tubular member having a lumen extending longitudinally therein.

The introducer 200 may include a sheath 230 and a sheath hub 232 extending over at least a portion of the pusher catheter 220. The sheath 230 may be configured as an elongate tubular member having a lumen extending longitudinally therein. The pusher catheter 220 may be slidably received within the lumen of the sheath 230. The sheath 230 may extend proximally from the sheath hub 232 to a proximal tip 240 of the introducer 200 for delivery of the prosthesis. The sheath 230 may be retracted relative to the pusher catheter 220 to at least partially expose the prosthesis retained below the sheath and positioned at a prosthesis retention section near the proximal end of the introducer 200 as further described below.

The introducer 200 may include an inner cannula 250. The inner cannula 250 may extend from a connector 252 (e.g., a Luer lock hub) positioned at the distal end of the introducer 200, through the handle 202 and the pusher catheter 220, and to the proximal tip 240. The inner cannula 250 may be configured as an elongate tubular member having a lumen extending longitudinally therein. The inner cannula 250 may be received within the lumen of the pusher catheter 220. The inner cannula 250 may extend at least partially through the proximal tip 240. The inner cannula 250 may be tracked over a guide wire in a conventional manner to guide the introducer 200 through the vasculature of the patient. The connector 252 may be used to introduce liquids such as contrast media to enable tracking of the progress of an operation.

In one example, the handle 202 may include a cannula handle 204 and a pusher handle 208 as shown in FIG. 3. The cannula handle 204 may be coupled to the inner cannula 250. Additionally, or alternatively, the pusher handle 208 may be coupled to the pusher catheter 220. The cannula handle 204 may be rotatable and/or translatable relative to the pusher handle 208. The inner cannula 250 may be rotated and/or translated relative to the pusher catheter 220 (e.g., by rotation and/or translation of the cannula handle relative to the pusher handle). The cannula handle 204 may be rotated (e.g., relative to the pusher handle 208) to rotate the inner cannula 250 for releasing a prosthesis as further described below. Rotation and/or translation of the cannula handle 204 relative to the pusher handle 208 may be inhibited by any suitable means. For example, the handle 200 may include a locking mechanism to inhibit rotation and/or translation of the cannula handle 204 relative to the pusher handle 208.

In another example, the handle 202 may be configured as a unitary handle coupled to the inner cannula 250 and/or the pusher catheter 220. The inner cannula 250 and the pusher catheter 220 may be rotated together (e.g., by rotation of the handle 202) to rotate the inner cannula for releasing the prosthesis. Alternatively, the inner cannula 250 may be rotated relative to the handle 202 and/or the pusher catheter 220 for releasing the prosthesis.

Figure 4:
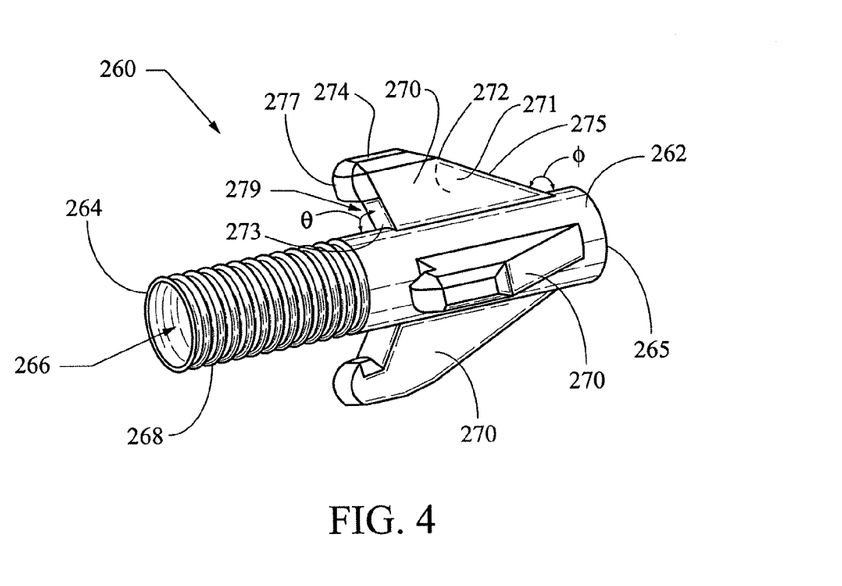
FIG. 4 illustrates the stent retaining member of the introducer of FIG. 3.

The introducer 200 may include a retaining member such as a stent retaining member 260 positioned at the prosthesis retention section. FIG. 4 illustrates one example of the stent retaining member 260. The stent retaining member 260 may include a sleeve 262 extending over at least a portion of the inner cannula 250. The sleeve 262 may be configured as a tubular member having a proximal end 264, a distal end 265, and a lumen 266 extending longitudinally within the sleeve. The inner cannula 250 may be received within the lumen 266 of the sleeve 262. The inner cannula 250 and the stent retaining member 260 may be rotatable and/or translatable relative to one another to deploy the prosthesis as further described below. The sleeve 262 may include an attachment mechanism such as a threaded segment 268 positioned at the proximal end 264 as shown in FIG. 4. The threaded segment 268 may include external threads positioned on the outer surface of the sleeve 262. The threaded segment 268 may engage the inner cannula 250 and/or the proximal tip 240 of the introducer 200 to releasably couple the stent retaining member 260 to the inner cannula as further described below. In other examples, the sleeve 262 may include any other type of attachment mechanism capable of releasably attaching the sleeve to the proximal tip as further described below.

In one example, the sleeve 262 may be configured as a torque shaft segment. To that end, the distal end 265 of the sleeve 262 may be positioned at the introduction portion (e.g., at the prosthesis retention section) near the proximal end of the introducer 200. Additionally, or alternatively, the distal end 265 of the sleeve may be positioned proximal of the proximal end of the pusher catheter 220 (e.g., between the pusher catheter and the distal end of the proximal tip 240) and/or proximal of the handle 202. The sleeve 262 may be unattached to the handle 202 of the introducer 200.

The stent retaining member 260 may include one or more engaging members such as one or more stent engaging members 270 extending radially from the sleeve 262. The stent engaging members 270 may be configured to engage a portion of the prosthesis to retain the engaged portion of the prosthesis in a compressed configuration. For example, each stent engaging member 270 may engage an apex of a stent (e.g., the stent 105 of the stent graft 100) as further described below. The stent engaging members 270 may be spaced from one another about the circumference of the sleeve 262. In one example, the stent retaining member 260 may include four stent engaging members 270 positioned approximately 90 degrees from one another about the circumference of the sleeve 262 as shown in FIG. 4. In other examples, the stent retaining member may include any number of stent engaging members spaced at any distance from one another about the circumference of the sleeve 262. In one example, the number of stent engaging members may be equal to one-half of the number of apices of the stent 105 of the stent graft 100. In this manner, the stent retaining member may be configured to engage every other apex of the stent 105 to retain the stent 105 in a partially expanded configuration as further described below. Alternatively, the number of stent engaging members may be equal to the number of apices of the stent 105. In this manner, the stent retaining member may be configured to engage every apex of the stent 105 to retain the stent 105 in the partially expanded configuration as further described below. In other examples, the stent retaining member may include any number of stent engaging members to engage any portion of a prosthesis.

Each stent engaging member 270 may be configured as a fin or rib extending longitudinally along the sleeve 262 and laterally or radially away from the sleeve as shown in FIG. 4. The stent engaging member 270 may be positioned longitudinally between the threaded segment 268 and the distal end 265 of the sleeve 262. Additionally, or alternatively, the distal end of the stent engaging member 270 may be substantially longitudinally aligned with the distal end of the sleeve. The stent engaging member 270 may include a relatively thin body having a first surface 271 and a second surface 272 positioned opposite the first surface. Each of the first surface 271 and the second surface 272 may extend along the length of the sleeve 262 and outward away from the sleeve. Each of the first surface 271 and the second surface 272 may be configured as a substantially planar surface. The first surface 271 and the second surface 272 may be substantially parallel to one another such that the thickness of the stent engaging member 270 is substantially constant along the length and the height of the stent engaging member. Alternatively, the first surface 271 and the second surface 272 may be non-parallel to one another such that the thickness of the stent engaging member 270 varies along the length and/or the height of the stent engaging member. In other examples, the first surface 271 and/or the second surface 272 may be non-planar. For example, the first surface 271 and/or the second surface 272 may be curved toward one another such that the thickness of the stent engaging member decreases in a radially outward direction.

The stent engaging member 270 may include a proximal edge 273, an outer edge 274, and a distal edge 275 as shown in FIG. 4. The proximal edge 273 and the distal edge 275 may be joined to one another by the outer edge 274. The proximal edge 273, the outer edge 274, and the distal edge 275 may collectively define an outer spine of the stent engaging member 270. The outer spine may extend between the first surface 271 and the second surface 272 of the stent engaging member 270.

The proximal edge 273 may include an inner end positioned adjacent to the sleeve 262 and an outer end opposite the inner end. The proximal edge 273 may extend outward away from the sleeve 262. Additionally, or alternatively, the proximal edge 273 may extend longitudinally relative to the sleeve 262. For example, the proximal edge 273 may extend radially outward and longitudinally in a proximal direction from the sleeve 262 such that an acute angle θ is formed between the proximal edge and the sleeve as shown in FIG. 4. Alternatively, the proximal edge may extend radially outward and longitudinally in a distal direction from the sleeve 262 such that an obtuse angle is formed between the proximal edge and the sleeve. In another example, the proximal edge may extend outward in a direction that is substantially perpendicular to the sleeve 262 such that a right angle is formed between the proximal edge and the sleeve 262.

The stent engaging member 270 may include a projection 277 extending from the proximal edge 273. The projection 277 may extend longitudinally from the proximal edge 273 in a proximal direction as shown in FIG. 4. The projection 277 may extend from the outer end of the proximal edge 273. The projection 277 may be configured to be received within a portion of a prosthesis to retain the prosthesis in a partially expanded configuration as further described below. A notch 279 may be positioned between the projection 277 and the outer surface of the sleeve 262. The notch 279 may have three sides defined by the sleeve 262, the proximal edge 273 of the stent engaging member 270, and the projection 277 (e.g., the radially innermost edge of the projection), respectively. The notch 279 may include an opening positioned radially between the proximal tip of the projection 277 and the sleeve 262. A portion of the prosthesis may be received within the notch 279 to retain the prosthesis in the partially expanded configuration as further described below.

The outer edge 274 may extend longitudinally relative to the sleeve 262 between the proximal edge 273 and the distal edge 275. In one example, the outer edge 274 may be substantially parallel to the outer surface and/or the longitudinal axis of the sleeve 262 as shown in FIG. 4. In other examples, the outer edge may be positioned at any angle relative to the sleeve 262. The outer edge 274 may define the radially outermost portion of the stent engaging member 270. To that end, the outer edge 274 may be joined to the outer end of the proximal edge 273 and the outer end of the distal edge 275. The outer edge 274 may be coextensive with the outer portion of the projection 277. In other words, the outer edge 274 may abut or define the radially outermost edge of the projection 277.

The distal edge 275 may include an inner end positioned adjacent to the sleeve 262 and an outer end opposite the inner end. The distal edge 275 may extend outward away from the sleeve 262. Additionally, or alternatively, the distal edge 275 may extend longitudinally relative to the sleeve 262. For example, the distal edge 275 may extend radially outward and longitudinally in a proximal direction such that an obtuse angle φ is formed between the distal edge and the sleeve 262 as shown in FIG. 4. In this manner, the distal edge 275 may form a tapered distal surface of the stent engaging member 270. Such a tapered distal surface may reduce the tendency of the stent engaging member 270 to catch or snag on a portion of the prosthesis or the introducer during deployment of the prosthesis as further described below. The distal edge 275 may extend in a substantially straight line from the inner end to the outer end of the distal edge. Alternatively, the distal edge may be curved between the inner end and the outer end of the distal edge. Such a curve may be concave or convex. In another example, the distal edge may extend radially outward and longitudinally in a distal direction such that an acute angle is formed between the distal edge and the sleeve 262. In another example, the distal edge may extend outward in a direction that is substantially perpendicular to the sleeve 262 such that a right angle is formed between the distal edge and the sleeve 262.

The stent engaging member 270 may be dimensioned to engage the stent 105 of the stent graft 100 as further described below. To that end, the stent engaging member 270 may have a thickness (e.g., between the first surface 271 and the second surface 272) between about 0.178 mm (0.007 in) and about 0.762 mm (0.03 in), typically between about 0.356 mm (0.014 in) and about 0.508 mm (0.02 in). Additionally, or alternatively, the stent engaging member 270 may have a length (e.g., between the inner end of the distal edge 275 and the proximal end of the projection 279) between about 1.25 mm and about 5.25 mm, typically between about 2.5 mm and about 3.5 mm. Additionally, or alternatively, the stent engaging member 270 may have a height (e.g., between the outer surface of the sleeve 262 and the outer edge 274) between about 1 mm and about 2 mm, typically between about 1.25 mm and about 1.5 mm. In other examples, the stent engaging member may have any size or shape suitable for engaging a prosthesis to retain at least a portion of the prosthesis in a partially expanded configuration.

Figure 5:
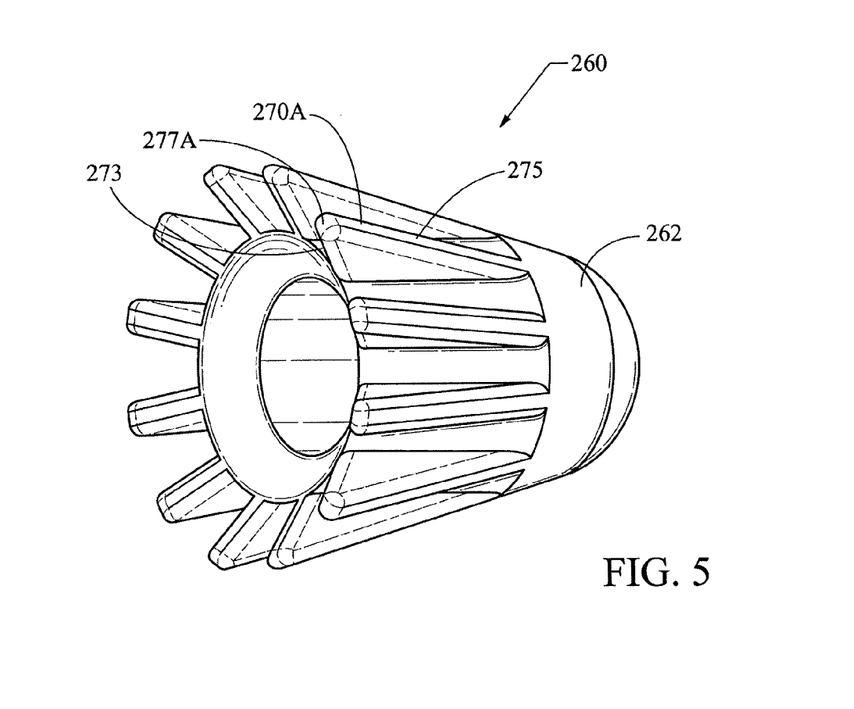
FIG. 5 illustrates another example of a stent retaining member.

FIG. 5 illustrates another example of the stent retaining member 260 including a stent engaging member 270A. The stent engaging member 270A may be similar to the stent engaging member 270 described above. For example, the stent engaging member 270A may include the proximal edge 273 and the distal edge 275. The outer edge 274 may be omitted such that the outer end of the proximal edge 273 and the outer end of the distal edge 275 meet one another to form a point 277A. The point 277A may be configured to engage a portion of a prosthesis as described herein with reference to the projection 277. The distal edge 275 may taper from the sleeve 260 to the point 277A. In one example, the distal edges 275 of a plurality of stent engaging members 270A may collectively form a frustoconical outer surface of the stent retaining member 260. Additionally, or alternatively, a distal portion of the sleeve 262 may be tapered as shown in FIG. 5. In one example, the taper of the proximal portion of the sleeve may be substantially the same as the taper of the distal edge 275. In this manner, a smooth taper may be formed from the distal end of the sleeve to the point 277A of the stent engaging member 270A. This may reduce the tendency of the stent retaining member 260 to snag on the deployed prosthesis during withdrawal as described herein. Additionally, or alternatively, the sleeve 262 of FIG. 5 may extend proximally beyond the point 277A to engage the proximal tip 240 and/or the inner cannula 250 as described above with reference to FIG. 4. Additionally, or alternatively, the sleeve 262 of FIG. 5 may include an attachment mechanism as described above with reference to FIG. 4.

The stent retaining member 260 shown in FIG. 5 may be made by forming a tubular member having a frustoconical shape. Such a tubular member may be formed, for example, by machining. The stent engaging members 270A may be formed by removing the portions of the frustoconical tubular member between adjacent stent engaging members. For example, portions of the tubular member may be removed by machining (e.g., electrical discharge machining (EDM) or wire EDM) to form the stent engaging members 270A. In this manner, the outer surfaces of the stent engaging members may have the frustoconical shape described above. Edges of the stent engaging members 270A may be machined to reduce the sharpness of the edges (e.g., to smooth the edges).

Figure 6:
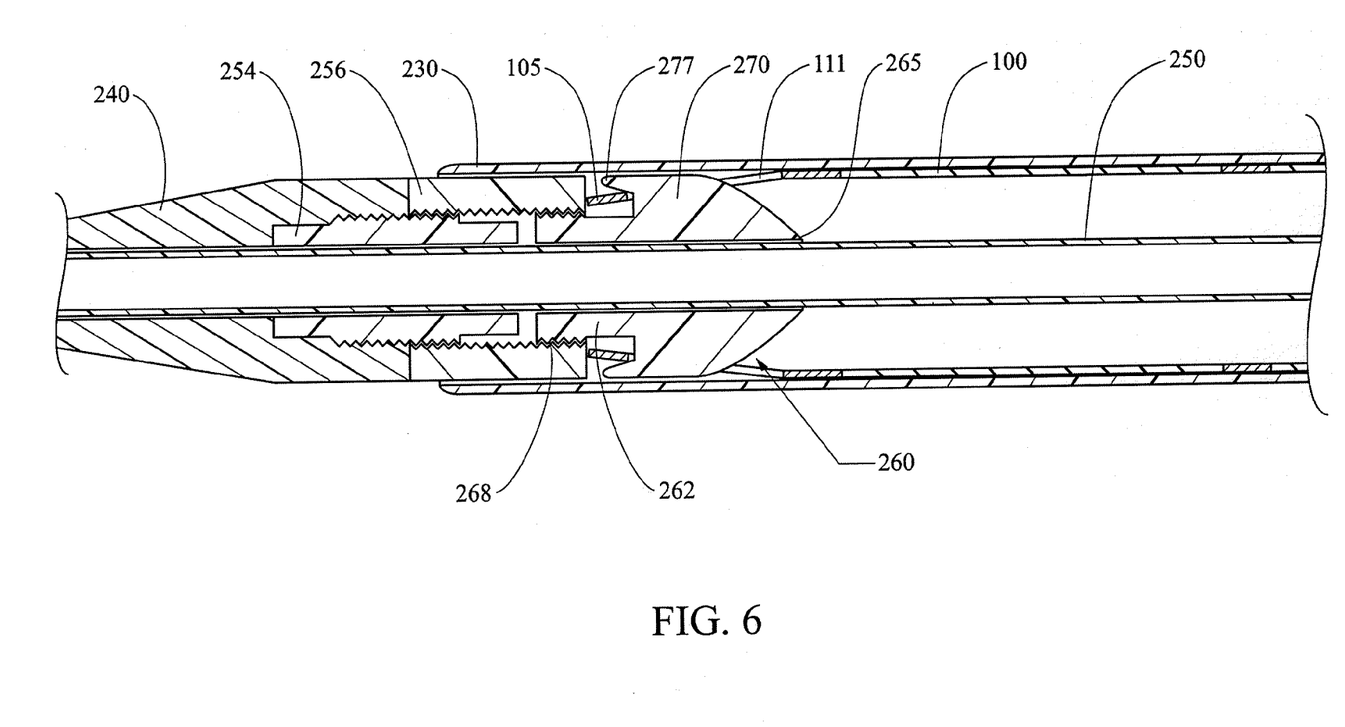
FIG. 6 is a longitudinal cross sectional view of a proximal portion of the introducer of FIG. 3 with the stent graft of FIG. 1 loaded on the introducer.

FIG. 6 is a partial longitudinal cross sectional view of a proximal portion of one embodiment of the introducer 200 with the stent graft 100 loaded on the introducer. The stent graft 100 may be positioned within the lumen of the sheath 230 in a conventional manner to retain the stent graft in a compressed, delivery configuration. The stent 105 of the stent graft 100 may be engaged by the stent retaining member 260 as further described below. The inner cannula 250 may include a threaded insert 254 attached to or integral with the proximal end of the inner cannula. The threaded insert 254 may include external threads configured to engage internal threads of the proximal tip 240 to couple the inner cannula 250 to the proximal tip. Additionally, or alternatively, the proximal tip 240 may be molded onto the inner cannula 250 and the threaded insert 254 to couple the inner cannula to the proximal tip. A coupling member 256 may be attached to the inner cannula 250 and/or the proximal tip 240 near the proximal end of the inner cannula. The coupling member 256 may be configured as a substantially cylindrical tubular member having internal threads. The coupling member 256 may be threadably engaged with the threaded insert 254 as shown in FIG. 6. The coupling member 256 and the proximal tip 240 may be joined to one another by the threaded insert 254 such that the coupling member forms a distal portion of the proximal tip to engage the stent 105 as further described below. Additionally, or alternatively, the distal end of the proximal tip 240 may include a threaded portion having external threads, and the internal threads of the coupling member 256 may be engaged with the external threads of the proximal tip. Additionally, or alternatively, the coupling member 356 may be integral with the proximal tip 240. In other words, the distal portion of the proximal tip 240 may include the coupling member 256.

The coupling member 256 may be fixedly attached (e.g., bonded or welded) to the threaded insert 254, the inner cannula 250, and/or the proximal tip 240. In this manner, rotation and/or translation of the inner cannula 250 and the proximal tip 240 relative to the stent retaining member 260 may cause a corresponding rotation and/or translation of the coupling member 256 relative to the stent retaining member. The coupling member 256 may extend distally to engage the stent retaining member 260. For example, the threaded segment 268 of the sleeve 262 of the stent retaining member 260 may be engaged with the internal threads of the coupling member 256 as shown in FIG. 6.

The stent retaining member 260 may engage the stent graft 100 to retain the stent graft in a partially expanded configuration after withdrawal of the sheath 230 as further described below. For example, the stent retaining member 260 may engage the stent 105 of the stent graft 100 as shown in FIG. 6. The stent engaging member 270 of the stent retaining member 260 may engage an apex of the stent 105. For example, the stent engaging member 270 may engage an opening or aperture of the apex, a bend of the apex positioned between two adjacent struts, or any other portion of the apex. The stent engaging member 270 of the stent retaining member 260 may extend through an opening in the stent 105. For example, the stent 105 may include one or more apertures 111 (e.g., eyelets) positioned near the proximal end of the stent as described above with reference to FIG. 2. The stent engaging member 270 may extend through the aperture 111 as shown in FIG. 6. The projection 277 of the stent engaging member 270 may be positioned radially outward of the stent 105. The proximal end 107 of the stent 105 may be positioned adjacent to or in abutting contact with the distal surface of the coupling member 256, which may form the distal surface of the proximal tip 240. In this manner, the engaged portion of the stent 105 may be prevented from moving proximally relative to the introducer 100 by the coupling member 256. The projection 277 of the stent engaging member 270 may be longitudinally aligned with at least a portion of the proximal portion of the stent 105. In other words, the projection 277 may hook the proximal end of the stent 105 as shown in FIG. 6. The proximal portion of the stent 105 (e.g., the portion of the stent positioned proximal of the aperture 111) may be at least partially positioned within the notch 279 of the stent engaging member 270. In this manner, the engaged portion of the stent 105 may be prevented from moving radially outward by the projection 277. The proximal portion of the stent 105 may be captured between the stent retaining member 260 and the coupling member 256. The other stent engaging members 270 of the stent retaining member 260 may engage other apices of the stent 105 in a similar manner. The stent engaging member 270 may push the slots and tips of the top stent (e.g., the stent 105) proximally and wedge them against the distal end of the coupling member 256 and/or the nose cone (e.g., the proximal tip 240). In one example, each apex of the stent 105 may be engaged by a corresponding stent engaging member 270. In other words, each apex of the stent 105 may be captured by the stent retaining member 260. In other examples, a portion of the apices (e.g., every other apex) of the stent may be engaged by a corresponding stent engaging member 270. The engaged apices may be prevented from moving radially outward relative to the stent retaining member 260 such that the stent 105 is prevented from expanding to a fully expanded configuration.

In other examples, the stent engaging member 170 may engage any other portion of the stent graft 100. For example, the stent engaging member 270 may extend through an opening between adjacent struts of the stent to engage the bend positioned between the struts. The stent retaining member 260 may be unattached to the handle 202 of the introducer 100. In one example, the distal end 265 of the sleeve 262 may be positioned within the lumen of the stent graft 100. In other words, the stent retaining member 260 may not extend distally beyond the distal end of the stent graft 100. In other examples, the sleeve may extend distally to the handle of the introducer as described below.

Figure 7:
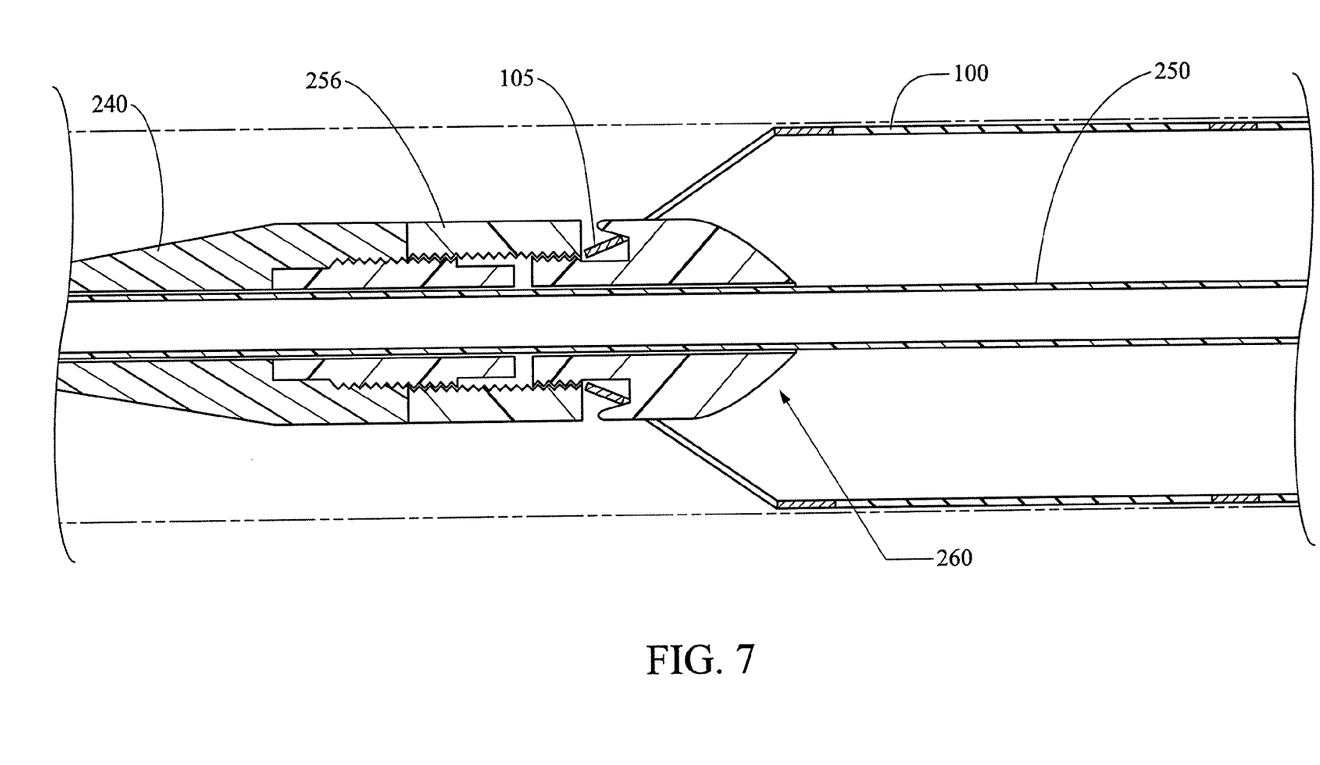
FIG. 7 is a longitudinal cross sectional view of the proximal portion of the introducer of FIG. 3 with a sheath retracted to partially deploy the stent graft.

The introducer 200 with the stent graft 100 loaded on the introducer may be advanced within a body vessel of a patient in a conventional manner to position the stent graft at a target location within the body vessel. The sheath 230 may be retracted distally relative to the inner cannula 250 to expose the stent graft 200 as shown in FIG. 7. Upon retraction of the sheath 230, the stent graft 100 may expand radially outward to a partially expanded configuration. For example, a distal portion of the stent graft 100 (e.g., the portion of the stent graft distal of the stent 105) may expand radially outward. The distal portion of the stent graft 100 may contact the wall of the body vessel as shown in FIG. 7. The stent 105 may remain engaged by the stent retaining member 260 as described above. In this manner, the stent 105 may be prevented from expanding to the fully expanded configuration. In other words, the stent 105 may not fully expand to engage the wall of the body vessel. This may enable repositioning of the stent graft 100 within the body vessel (e.g., by translating the introducer 100 proximally or distally relative to the body vessel) prior to complete deployment of the stent graft.

The stent 105 may be released from the stent retaining member 260 to fully deploy the stent graft 100. In one example, the inner cannula 250 may be rotated relative to the stent graft 100. The inner cannula 250 may be rotated by rotating the handle 202 of the introducer 200. Such rotation of the inner cannula 250 may cause a corresponding rotation of the coupling member 256. The inner cannula 250 may be rotatably and slidably received within the lumen 266 of the sleeve 262 of the stent retaining member 260 as described above. Upon rotation of the inner cannula 250 and the coupling member 256, the stent retaining member 260 may be substantially prevented from rotating by the engagement between the stent retaining member and the stent 105. In other words, the engagement (e.g., the frictional force) between the distal portion of the stent graft 100 and the wall of the body vessel may substantially prevent the stent graft 100 from rotating within the body vessel, and the engagement between the stent 105 and the stent retaining member 260 may substantially prevent the stent retaining member 260 from rotating relative to the stent graft. The position of the stent retaining member 260 may be substantially fixed relative to the engaged stent graft 100. Rotation of the inner cannula 250 and the coupling member 256 relative to the stent graft 100 may cause a corresponding rotation of the inner cannula and the coupling member relative to the stent retaining member 260.

Figure 8:
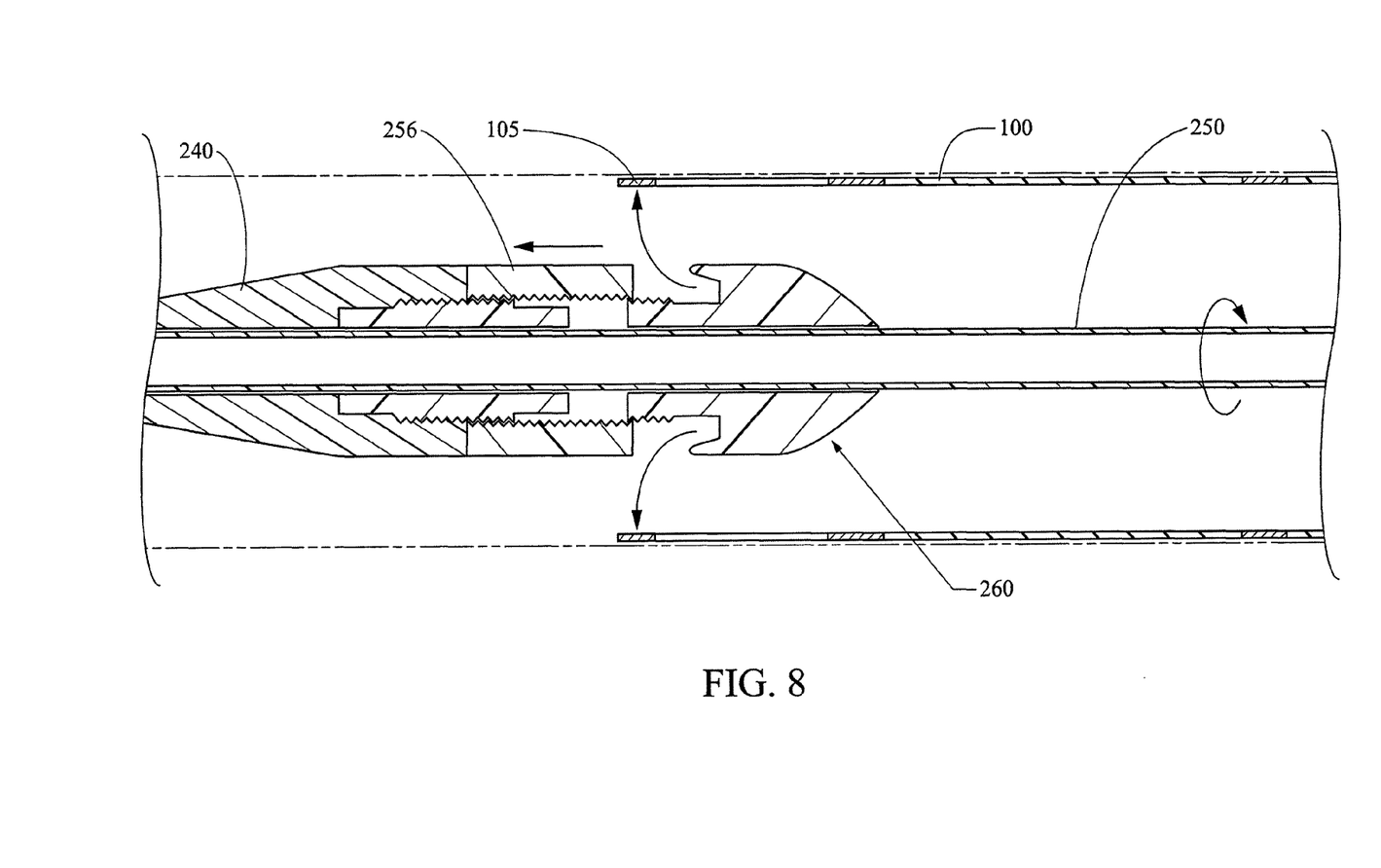
FIG. 8 is a longitudinal cross sectional view of the proximal portion of the introducer of FIG. 3 with the stent graft fully deployed.

Upon rotation of the coupling member 256 relative to the stent retaining member 260, the coupling member and the sleeve 262 of the stent retaining member may unthread from one another. Such unthreading may cause the coupling member 256 to move proximally relative to the stent retaining member 260 as shown in FIG. 8. The inner cannula 250, the coupling member 256, and the proximal tip 240 may move proximally as a unit relative to the stent retaining member 260. Upon proximal movement of the coupling member 256 relative to the stent retaining member 260, the distance between the distal face of the coupling member and the stent engaging member 270 may increase. The coupling member 256 may be rotated relative to the stent retaining member 260 until the engaged proximal portion of the stent 105 is capable of passing through the space between the projection 277 of the stent engaging member 270 and the distal face of the coupling member 256. In other words, the coupling member 256 may be rotated relative to the stent retaining member 260 until the distance between the distal face of the coupling member and the stent engaging member 270 is sufficient to release the stent 105 of the stent graft 100.

In one example, in response to rotation of the inner cannula 250 with respect to the stent retaining member 260, the proximal tip 240 (e.g., the coupling member 256 of the proximal tip) may be longitudinally movable relative to the stent engaging member 270 between a retaining configuration as shown in FIGS. 6-7 and a releasing configuration as shown in FIG. 8. The longitudinal distance between the stent engaging member 270 and the proximal tip 240 in the retaining configuration may be less than the longitudinal distance between the stent engaging member and the proximal tip in the releasing configuration. In other words, the proximal tip 240 and the stent engaging member 270 may be spaced from one another by a greater longitudinal distance in the releasing configuration than in the retaining configuration. In this manner, the stent engaging member 270 and the proximal tip 240 in the retaining configuration may be configured to capture and/or retain the stent 105. Additionally, or alternatively, the stent engaging member 270 and the proximal tip 240 in the releasing configuration may be configured to release the stent 105.

Upon release from the stent retaining member 260, the stent 105 may expand to the expanded configuration to engage the wall of the body vessel. The threaded segment 268 of the sleeve 262 of the stent retaining member 260 may have a sufficient length that the stent retaining member and the coupling member 256 may remain engaged with one another after release of the stent 105 as shown in FIG. 8. This may prevent the stent retaining member 260 from translating freely (e.g., sliding proximally and/or distally) along the inner cannula 250 after release of the stent 105. Alternatively, the stent retaining member 260 and the coupling member may be disengaged from one another following release of the stent 105. Additionally, or alternatively, the threaded segment 268 may have a sufficient length that the engagement (e.g., the threaded engagement) between the retaining member 260 and the coupling member 256 is sufficiently strong to withstand longitudinal pulling forces which may be experienced during loading and/or deployment of the stent graft 100.

While FIGS. 6-8 show a stent retaining member configured generally as described in FIG. 4, the principles described in connection with FIGS. 6-8 are equally applicable to introducer embodiments with stent retaining members and/or coupling members having different configurations such as, for example, those shown in FIG. 5.

In any of the embodiments described herein, the retaining member and the coupling member may be formed from any suitable material. The retaining member and the coupling member may be formed from the same or different materials. In one example, the retaining member and/or the coupling member may be formed from stainless steel. The retaining member and/or the coupling member may be formed using any suitable process such as, for example, machining or stamping. Using a stamping process may reduce the cost of producing and/or assembling the introducer. The retaining member or a portion thereof (e.g., the engaging members) may be heat treated to increase the strength of the retaining member. In other examples, the retaining member and the coupling member may be formed from any other suitable materials such as, for example, metallic materials or polymeric materials.

II. Loading Tools

The attachment stent 105 of the stent graft 100 may be difficult to load onto or engage with the introduction portion 203 of the introducer 200. For example, the apices of the attachment stent 105 may need to be engaged with the stent engaging members 270 one at a time by hand. Thus, keeping apices that have been engaged with the stent engaging members 270 while engaging the other apices with stent engaging members 270 may be difficult. While engaging four to six apices may be done by hand, as the number of apices that need to be engaged increases, the difficulty of doing so by hand increases. For example, engaging apices to the four stent engaging members 270 of the stent retaining member 260 of FIG. 4 may be done relatively easy by hand, while engaging the apices to the twelve stent engaging members 270A of the stent retaining member 260 of FIG. 5 may be more difficult. In particular, the apices are generally compressed when engaged with the stent engaging members 270, so apices generally disengage from the stent engaging members 270 unless held down or have been captured by the stent retaining member 260. In addition, in order to capture the apices, each of the apices that are intended to be engaged with the stent retaining member 260 may need to be engaged prior to engaging the stent retaining member 260 and the coupling member 256. For instance, when engaging the stent retaining member 260 with the coupling member 256, each of the apices may be captured substantially simultaneously. Thus, each of the apices may need to be maintained engaged with the stent engaging members 270 during engagement of the stent retaining member 260 with the coupling member 256 to be able to capture all of the apices.

When the stent 105 has a relatively large number of apices, fewer than all of the apices may be captured by stent retaining member 260, such as four of eight apices may be captured. For example, when the apices are loaded by hand, a fraction of the total number of apices may be chosen to be captured at least in part due to the difficulty of being able to have all the apices engaged with the stent retaining member 260 at the same time. Thus, some of the apices may not be captured by the stent retaining member 260. Instead, the sheath 230 may retain the non-captured apices. However, when the sheath 230 is removed, the non-captured apices may radially extend away from the introducer 200, and the apices may immediately engage with a vessel wall of a patient. The engagement of the apices with the vessel wall may be particular prevalent when the apices include barbs. Thus, if the physician does not deploy the stent 105 at the correct location in the vessel, the stent 105 may not be able to be moved or adjusted. Furthermore, during adjustment of the stent graft 100, the stent graft 100 may be moved proximally. When the introducer 200 is moved proximally, the captured apices are moved proximally, which may result in the non-captured apices moving radially further away from introducer 200 and closer to vessel walls. Therefore, if all of the apices are instead captured by the stent retaining member 260, the stent graft may be easier to adjust after the sheath 230 is removed. In addition, the adjustment of the stent graft 100 may create substantial stresses on the captured apices, while the non-captured apices may not experience substantial stresses from the adjustment. Thus, when more of the apices are captured, more apices may share the forces generated by the adjustment, and the maximum stress that any one of the apices experiences is reduced. The reduced maximum stress that the apices experience may reduce the likelihood of bending of the apices during adjustment.

Figure 9:
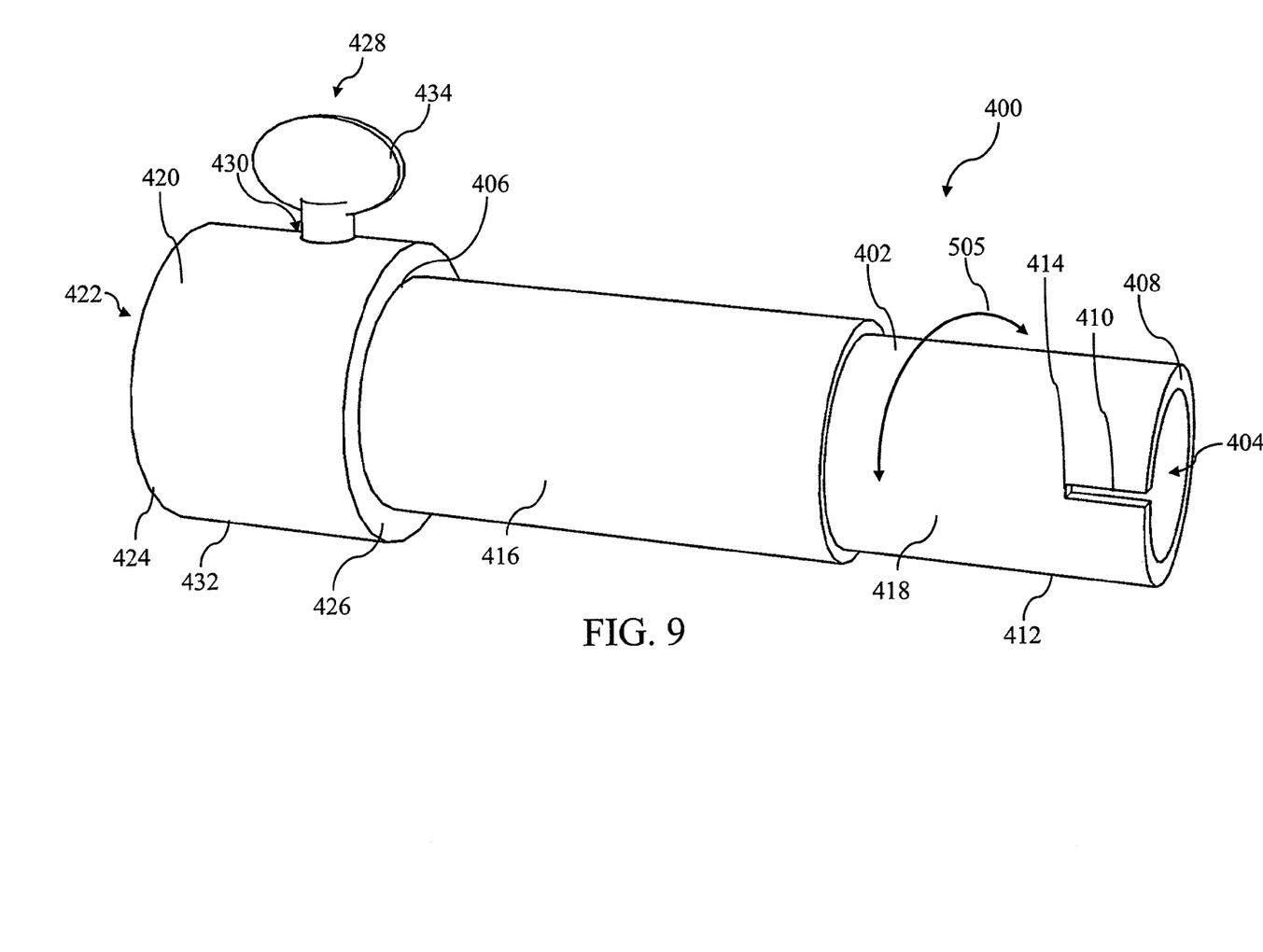
FIG. 9 is a perspective view of one example of a loading tool.

FIG. 9 depicts one example of a loading tool 400 for engaging apices of a stent 105 on the stent engaging member 270. The loading tool 400 may include a loading body 402 having a passage 404 extending from a first end 406 to a second end 408. The loading body 402 may further include a slot 410 that extends through the loading body 402 from the passage 404 to an outer surface 412 of the tubular loading body 402 and may extend from the second end 408 toward the first end 406. In order to use the loading tool 400, the second end 408 may be slid over the proximal tip 240 of the introducer 200 such that the proximal tip 240 enters the passage 404 of the loading body 402. The loading tool 400 may continue to be slid over introducer until the slot 410 is adjacent to or neighbors the stent engaging member 270. Alternatively, the loading body 402 may include a hinge to open the passage 404. For example, the loading body 402 may include a hinge and a slit that extend longitudinally along the loading body 402 so that the slit may be opened by rotating portions of the loading body 402 about the hinge to expose the passage 404. The loading body 402 may then be placed over the introducer 200 and the slit may be closed thereby enclosing the introducer 200 within the passage 404.

Figure 10:
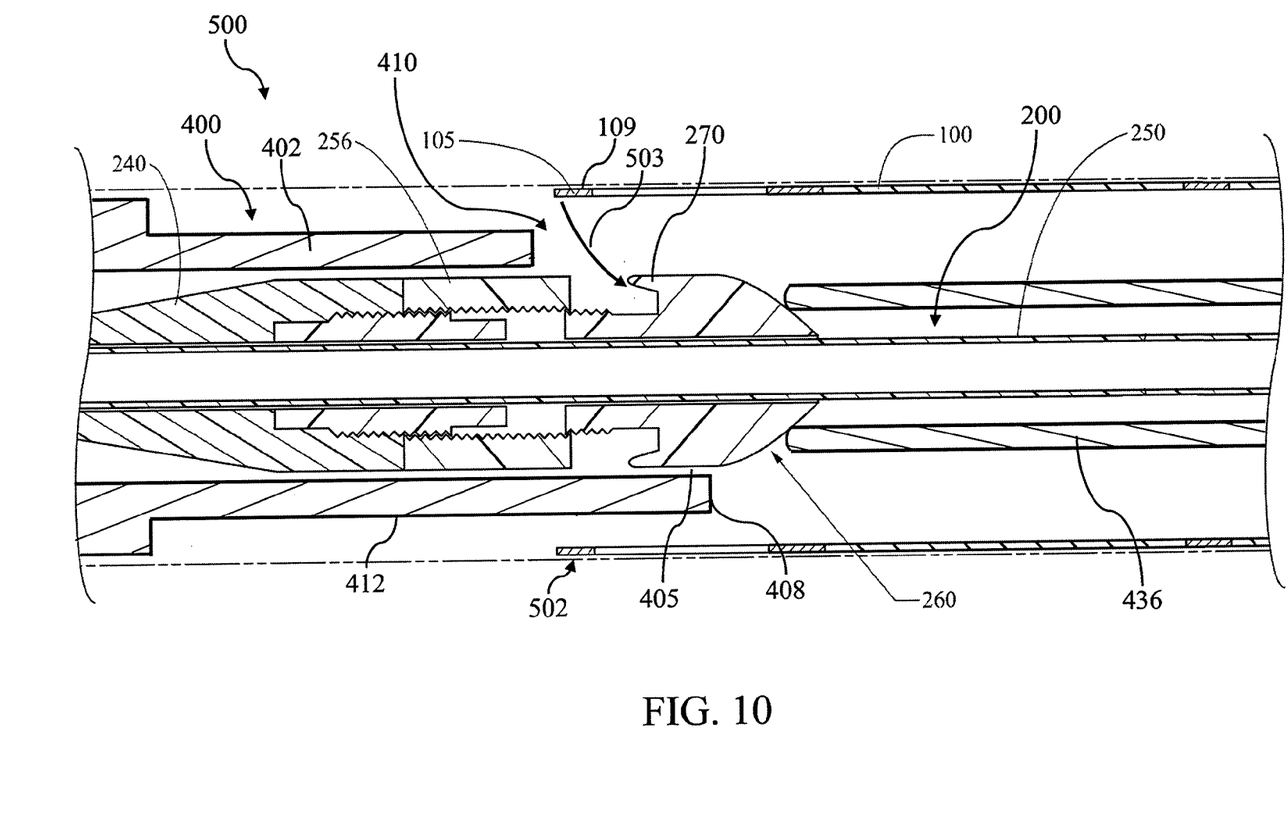
FIG. 10 is a cross sectional view of a system that includes an introducer and a loading tool.

FIG. 10 depicts a cross-sectional view of one embodiment of a system 500 that may include the loading tool 400. The system 500 may also include an endoluminal prosthesis introducer 200 that includes an engaging member 260 engageable with a stent end 502 in a compressed configuration. The cross-sectional view depicted in FIG. 10 is through the slot 410, and the slot 410 is radially aligned with one of the stent engaging members 270 of the stent retaining member 260. Furthermore, the system 500 in FIG. 10 is also depicted so that one of the apices of the stent 105 is also radially aligned with the slot 410 along with the stent engaging member 270 that is radially aligned with the slot 410. Radial alignment may generally refer to elements residing along a common straight line that extends from and is perpendicular to an axis of the introducer 200 such as an axis of the stent retaining member 260 or the inner cannula 250. For example, aligned elements may each reside along a radial path extending from the axis of the introducer 200.

The slot 410 may be configured to allow an apex of the stent 105 to pass though the slot 410 such that the apex may be moved from being outside of the passage 404 of the loading body 402 to being within the passage 404. FIG. 10 includes an arrow 503 to indicate the movement path of the apex. The apex may thereby be engaged one of the stent engaging members 270, as described above in Section I. After the apex is engaged with the stent engaging member 270, the loading body 402 may be rotated about an axis of the introducer 200. For example, with the apex of the stent end 502 engaged with the stent engaging member 270, the slot 410 can be movable to a misaligned position, whereby the apex is retained within the passage 404 of the loading body 402. FIG. 9 includes an arrow 505 to indicate rotation of the loading body 402. The loading body 402 may be rotated such that a second apex to be engaged with a second stent engaging member 270 is aligned with the slot 410. For example, the slot 410 may be aligned with a stent engaging member 270 that is adjacent to or neighbors the stent engaging member 270 that previously had an apex engage thereto. The second apex and the second stent engaging member 270 may be engaged, and then the loading body 402 may be rotated again. Thus, the slot 410 may be rotated about stent retaining member 260, stopping sequentially to be aligned with each stent engaging member 270 so that an apex of the stent 105 may be engaged with the corresponding stent engaging member 270. As such, the loading body 402 can be configured to be sequentially rotated so that the slot 410 is movable into radial alignment with each of the stent engaging members 270. The portion of the loading body 402 that is adjacent to the second end 408 that does not form the slot 410 may prevent the apices from disengaging with the engaging members 270. For example, the loading body 402 may restrict radial movement of the apices. For instance, the apices may be sandwiched between loading body 402 and the stent retaining member 260. Thus, the stent retaining member 260 may include a relatively large number of stent engaging members 270, such as at least eight stent engaging members 270, where each stent engaging member 270 is configured to engage with an apex of the stent end 502.

After each of the apices is engaged with a corresponding stent engaging member 270, as described above in Section I, the inner cannula 250 may be rotated relative to the stent 105 so that the stent retaining member 260 engages with the coupling member 256 in order to capture the apices with the stent engaging members 270. For example, the stent engaging member 270 may longitudinally move from the releasing configuration to the retaining configuration. After the apices of the stent 105 are captured, the loading tool 400 may be removed from the introducer 200, and the introducer 200 and the stent 105 may have a configuration as depicted in FIG. 7.

The slot 410 of the loading tool 400 may extend from the second end 408 to a position 414 between the first end 406 and the second end 408. For example, the position 414 may be selected so that an apex may pass through the slot 410. Generally, the position 414 may be further from the second end 408 than necessary for the apex to pass through the slot 410. The width of the slot 410 may also be selected so that an apex may pass through the slot 410. The width of the slot 410 may be substantially the same as or slightly larger than the width of the apex. If the width of the slot 410 is much larger than the width of the apex, keeping the apices within the passage 404 of the loading body 402 may be more difficult. For example, the width of the slot 410 may be greater than the width of the apex and less than about two times the width of the apex. Although the slot 410 is depicted in FIG. 9 as being rectangular, the slot 410 may have other configuration such as having a wedge shape that corresponds to or matches the shape of the apex. A portion of the loading body 402 that extends from the second end 408 to the position 414 may form an annulus with the slot 410 being a discontinuity. Furthermore, the slot 410 may be the only discontinuity of the annulus. Thus, the portion of the loading body 402 that extends from the second end 408 to the position 414 may at least partially cover all of the stent engaging members 270 except for the stent engaging member 270 that is radially aligned with the slot 410. In addition, a portion of the loading body 402 that extends from the first end 406 to the position 414 may form a substantially continuous annulus.

A diameter of the passage 404 at the second end 408 may be substantially the same or slightly larger than an outer diameter of the stent retaining member 260. For instance, a gap 405 between the passage 404 and the stent engaging members 270 may be less than the thickness of the apices so that the apices may not move though the gap 405 and apices may be retained between the loading body and the engaging member. For example, passage 404 may have a diameter that is about 0.25 mm to about 0.40 mm larger than the outer diameter of the stent retaining member 260.

The loading body 402 may be formed of any one of various materials such as polymers and metals. For example, the loading body 402 may be formed of nylon, polyethylene or steel. The loading body 402 at the second end 408 may have a wall thickness that may be sufficient to retain loaded apices within the passage 404. The wall thickness at the region adjacent to the second end 408 may be, for example, about 0.5 mm to about 2.0 mm. A relatively thin wall thickness adjacent to the slot 410 may improve the ability to manipulate an apex through the slot 410. FIG. 9 depicts the loading body 402 having a first section 416 and a second section 418 with different outer diameters that are adjacent to one another along the length of the loading body 402. The first section 416 extends from the first end 406 to the second section 418, and the second section 418 extends from the second end 408 to the first section 416. The wall thickness of the second section 418 may be less than the wall thickness of first section 416 so that an apex may be more easily manipulated through the slot 410. The first section 416 may have a larger wall thickness than the second section 418 to provide additional structural support to the second section 418. In addition, the first section 416 may have a larger outer diameter than the second section 418 to enable the first end 406 to be coupled to a hub 420, as described below.

The loading tool 400 may include a hub 420 rotatably attached to the first end 406 of the loading body 402. The hub 420 may also have a passage 422 extending from a first end 424 to a second end 426 of the hub 420. The passage 422 of the hub 420 together with the passage 404 of the loading body 402 may form a continuous passage though the loading tool 400.

The hub 420 may include a coupling mechanism 428 that is engageable with the introducer 200 to fix the hub 420 in place relative to the introducer 200. For example, the coupling mechanism 428 may include a threaded hole 430 extending through the hub 420 from an outer surface 432 to the passage 404. A screw 434 such as a set screw or a wing tip screw may engage with the threaded hole 430 and extend through the threaded hole 430 to engage the introducer 200. The screw 434 may be tightened onto the introducer 200 to fix the hub 420 to the introducer 200. Alternatively, one or more other coupling mechanisms 428 may be used such as an elastic band or a friction fitting.

The first end 406 of the loading body 402 may be rotatably attached to the hub 420 by any one of various methods. For example, the hub 420 and the first end 406 may form an annular snap joint such that one of the hub 420 and the first end 406 includes an annular groove within the passageway, and the other of the hub 420 and the first end 406 includes a protrusion on an outer surface that engages with the groove. Alternatively, a ball bearing may couple the hub 420 to the first end 406. Furthermore, the hub 420 may be configured to rotate in both directions. Alternatively, the hub 420 may be configured to rotate in only one direction. For example, the hub 420 may include a ratcheting mechanism.

The hub 420 may assist in being able to rotate the loading body 402 relative to the introducer 200. For instance, if the hub 420 is fixed to the introducer 200, the loading body 402 is restricted from moving longitudinally along the introducer 200. After each of the apices is engaged with a corresponding stent engaging member 270, the hub 420 may also assist with engaging the stent retaining member 260 and the coupling member 256. For example, the hub 420, while fixed to the introducer 200, may be rotated thereby rotating the inner cannula 250 to capture the apices with the stent engaging members 270.

As depicted in FIG. 10, the system 500 may also include a friction member 436 that restricts movement of the stent retaining member 260. For example, the friction member 436 may be a tubular member that slides over the distal end of the introducer 200 and is positioned between the inner cannula 250 and the stent 105. Alternatively, the friction member 436 may include a longitudinal hinge feature to open the tubular member as described above with regard to the loading body 402. A proximal end of the friction member 436 may be pressed against the distal end of the stent retaining member 260 thereby restricting rotational movement of the stent retaining member 260. By restricting rotational movement of the stent retaining member 260, alignment of the stent engaging member 270 with the slot 410 may be more easily maintained. The friction member 436 may be a separate component from the loading tool 400 so that the loading body 402 may be rotated relative to the friction member 436.

After the stent 105 is loaded onto the introducer 200, the loading tool 400 can be removed from the introducer 200. For example, if the hub 420 is engaged with the introducer 200, the hub 420 can be disengaged with the introducer 200. The loading tool 400 can then be slid off of the proximal tip 240 of the introducer 200.

While the loading tool 400 may have been described in relation to an example introducer 200 and stent graft 100, the loading tool 400 may be used with various other introducers and stents. For example, a system may include any of the prostheses and introducers described in U.S. patent application Ser. No. 13/669,145, entitled "ENDOLUMINAL PROSTHESIS INTRODUCER," filed Nov. 5, 2012, which is incorporated by reference herein in its entirety. Furthermore, a system may include a delivery system that has coiled member such as those described in U.S. Provisional Patent Application Ser. No. 61/659,255, entitled "SYSTEMS AND METHODS FOR DEPLOYING A PORTION OF A STENT USING AT LEAST ONE COILED MEMBER," filed Jun. 13, 2012, which is incorporated by reference herein in its entirety. For example, the loading tool 400 may be used to assist with engagement of apices of a stent end with the coiled member.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system comprising:
   an endoluminal prosthesis introducer comprising a stent retaining member engageable with a stent end in a compressed configuration; and
   a loading tool to facilitate engaging the stent end on the stent retaining member comprising a loading body having a passage extending from a first end to a second end and a slot that extends through the loading body from the passage to an outer surface of the tubular loading body, the slot extending from the second end toward the first end,
   wherein the stent retaining member is disposed at least partially within the passage of the loading body, and the slot of the loading body is rotatable around the stent retaining member.

2. The system of claim 1, wherein the loading tool comprises a hub rotatably attached to the first end of the loading body.

3. The system of claim 2, wherein the hub comprises a coupling mechanism that is engageable with the introducer to fix the hub in place relative to the introducer.

4. The system of claim 3, wherein the hub comprises a hub passage extending from a first end to a second end of the hub, and the coupling mechanism comprises a screw that is extendable through the hub from an outer surface of the hub and into the hub passage to engage the introducer.

5. The system of claim 1, wherein the introducer comprises a proximal tip positioned proximal of the engaging member, and the proximal tip is disposed at least partially within the passage of the loading body.

6. The system of claim 5, wherein the stent retaining member is longitudinally movable relative to the proximal tip within the loading body between a releasing configuration and a retaining configuration.

7. The system of claim 6, wherein the introducer comprises an inner cannula, the proximal tip is attached to a proximal end of the inner cannula, and the stent retaining member is disposed circumferentially around the inner cannula.

8. The system of claim 1, wherein the stent retaining member comprises a plurality of stent engaging members disposed circumferentially about a longitudinal axis of the introducer.

9. The system of claim 8, wherein the loading body is sequentially rotatable so that the slot is movable into radial alignment with each of the stent engaging members.

10. The system of claim 9, wherein, when the slot is radially aligned with one of the plurality of stent engaging members, an apex of the stent end is movable radially inward through the slot and engageable with the engaging member.

11. The system of claim 8, wherein the stent engaging members comprise fins extending outward away from the axis of the introducer.

12. The system of claim 11, wherein the stent end comprises a plurality of apices having an aperture engageable with the fins.

13. The system of claim 8, wherein the plurality of stent engaging members comprises at least eight stent engaging members, and each is engageable with an apex of the stent end.

14. A method of loading a stent end onto an endoluminal prosthesis introducer, the method comprising:
   providing an endoluminal prosthesis introducer comprising a stent retaining member engageable with a stent end in a compressed configuration;
   positioning a loading tool comprising a loading body having a passage extending from a first end to a second end such that the engaging member is disposed at least partially within the passage of the loading body, the loading body comprising a slot that extends through the tubular loading body from the passage to an outer surface of the tubular loading body, and the slot extending from the second end toward the first end; and
   rotating the slot of the loading body around the stent retaining member.

15. The method of claim 14, further comprising removably fixing a hub to the introducer, wherein the hub is rotatably attached to the first end of the loading body.

16. The method of claim 14, wherein the stent retaining member comprises a plurality of stent engaging members disposed circumferentially about a longitudinal axis of the introducer.

17. The method of claim 14, wherein the stent end comprises a plurality of apices, and the method further comprises engaging a first apex of the plurality of apices with a first engaging member of the plurality of stent engaging members when the slot is radially aligned with the first engaging member.

18. The method of claim 17, further comprise rotating the slot to misalign the slot with the first engaging member to retain the first apex between the loading body and the first engaging member.

19. The method of claim 18, further comprises engaging a second apex of the plurality of apices with a second engaging member of the plurality of stent engaging members when the slot is radially aligned with the second engaging member.

20. A loading tool to facilitate engaging a stent end on a stent retaining member comprising:
   a loading body having a passage extending from a first end to a second end and a slot that extends through the loading body from the passage to an outer surface of the tubular loading body, the slot extending from the second end toward the first end,
   wherein a stent retaining member is positionable at least partially within the passage of the loading body, and the slot of the loading body is rotatable around the stent retaining member.

* * * * *